(12) United States Patent
Meng et al.

(10) Patent No.: US 12,429,457 B2
(45) Date of Patent: Sep. 30, 2025

(54) REAL-TIME ULTRASONIC STIMULATION ELECTRIC SIGNAL RECORDING CHIP AND PREPARATION METHOD THEREOF

(71) Applicant: SHENZHEN INSTITUTES OF ADVANCED TECHNOLOGY CHINESE ACADEMY OF SCIENCES, Shenzhen (CN)

(72) Inventors: Long Meng, Shenzhen (CN); Wei Zhou, Shenzhen (CN); Hairong Zheng, Shenzhen (CN); Lili Niu, Shenzhen (CN); Zhengrong Lin, Shenzhen (CN); Benxian Peng, Shenzhen (CN); Farooq Umar, Shenzhen (CN); Yingjian Cui, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 390 days.

(21) Appl. No.: 18/332,697

(22) Filed: Jun. 9, 2023

(65) Prior Publication Data

US 2023/0314377 A1 Oct. 5, 2023

Related U.S. Application Data

(63) Continuation of application No. PCT/CN2020/135475, filed on Dec. 10, 2020.

(51) Int. Cl.
*G01N 29/02* (2006.01)
*H03H 3/10* (2006.01)
(Continued)

(52) U.S. Cl.
CPC ............. *G01N 29/022* (2013.01); *H03H 3/10* (2013.01); *H03H 9/02574* (2013.01); *H03H 9/25* (2013.01)

(58) Field of Classification Search
CPC .... G01N 29/022; H03H 3/10; H03H 9/02574; H03H 9/25; A61N 7/00; A61N 2007/0026; A61B 2562/12
See application file for complete search history.

(56) References Cited

U.S. PATENT DOCUMENTS 9,593,808 B1 *   3/2017  Gaitas ............. G01N 33/54366
2011/0257501 A1 * 10/2011 Huys ................... A61B 5/4041
                                                            600/377
(Continued)

FOREIGN PATENT DOCUMENTS

CN    106037723 A    10/2016
CN    106390306 A     2/2017
(Continued)

*Primary Examiner* — Francis C Gray
(74) *Attorney, Agent, or Firm* — Nitin Kaushik

(57) ABSTRACT

The present invention discloses a real-time ultrasonic stimulation electric signal recording chip and a preparation method thereof, where the preparation method includes the following steps: S1 manufacturing an interdigital electrode on a piezoelectric substrate to obtain a surface acoustic wave chip, and manufacturing a recording electrode and an electrode lead; S2, manufacturing an insulation protection layer on the chip obtained in the S1, and processing the insulation protection layer to form the recording electrode, so as to obtain a chip combining the interdigital electrode and the recording electrode; S3, preparing a PDMS cavity; and S4, bonding the PDMS cavity prepared in the S3 and the chip obtained in the S2. In the present invention, combining the interdigital electrode generating a surface acoustic wave ultrasound with a multi-channel recording electrode, such (Continued)

that real-time recording of a multi-channel electric signal under ultrasonic stimulation is achieved.

10 Claims, 3 Drawing Sheets

(51) Int. Cl.
    *H03H 9/02*     (2006.01)
    *H03H 9/25*     (2006.01)

(56) References Cited

U.S. PATENT DOCUMENTS

| | | |
|---|---|---|
| 2016/0271427 A1 | 9/2016 | Lal |
| 2017/0108926 A1 | 4/2017 | Moon et al. |
| 2020/0114175 A1* | 4/2020 | Maharbiz ............ A61B 8/4483 |

FOREIGN PATENT DOCUMENTS

| | | | | |
|---|---|---|---|---|
| CN | 106390306 B | * | 7/2019 | ............... A61N 7/00 |
| CN | 109985672 A | | 7/2019 | |
| KR | 20130101604 A | | 9/2013 | |

* cited by examiner

REAL-TIME ULTRASONIC STIMULATION ELECTRIC SIGNAL RECORDING CHIP AND PREPARATION METHOD THEREOF

TECHNICAL FIELD

The present invention belongs to the technical field of neuromodulations, in particular, relates to a real-time ultrasonic stimulation electric signal recording chip and a preparation method thereof.

BACKGROUND

For a long time, mental diseases such as motility disorders, pain, epilepsy, Parkinson's disease, mental illness and angina pectoris seriously affect the health and quality of life of human beings. Despite the continuous application of new antipsychotic drugs in clinical practice, a significant proportion of patients remain insensitive or unsatisfactory to drug treatment. A neuromodulation therapeutic method belongs to a more popular therapeutic method in recent years, has a good therapeutic effect on various nerve diseases, and has a high development speed.

The neuromodulation is a biomedical engineering technology which plays a role in exciting, inhibiting or regulating neurons or nerve signal transduction at adjacent or distant parts of a central nervous system, a peripheral nervous system and an autonomic nervous system through an implantable or non-implantable technology and an electric or chemical action mode so as to achieve aims of improving the life quality of the patients and improving the nerve function.

The ultrasonic neuromodulation is a neuromodulation means proposed in recent years, that can non-invasively penetrate through a skull to regulate and control a nerve nucleus of a brain, and has attracted wide attention in the aspect of treating diseases such as Parkinson, and epilepsy, but a mechanism of the ultrasonic neuromodulation is not clear. The nerve signal is an electric signal, and the signal shows potential change when being transmitted on the nerve, so a record of the electric signal can effectively represent a response of a neuron under an ultrasonic action so as to research the mechanism of the ultrasonic neuromodulation. However, a currently commercial ultrasonic transducer has a huge volume, and is difficult to be compatible with an electrophysiological means, such as calcium imaging, patch clamp and other electric signal recording means, a sound field of a traditional ultrasonic transducer is not uniform, and ultrasonic stimulation energy of the recorded neuron is seriously dependent on a relative position of the recorded neuron and the transducer, such that a result is difficult to repeat. Therefore, it is very necessary to develop a chip which has uniform ultrasonic energy and easy operation and can realize real-time recording of a neuron electric signal under the ultrasonic stimulation.

SUMMARY

In view of the above problems, the present invention provides a preparation method for a real-time ultrasonic stimulation electric signal recording chip, which combines an interdigital electrode with a recording electrode to form a chip and bonds a PDMS cavity, such that real-time recording of an electric signal under ultrasonic stimulation is achieved.

Another aim of the present invention is to provide the real-time ultrasonic stimulation electric signal recording chip prepared by the above preparation method.

The technical solution adopted by the present invention is as follows.

A preparation method for a real-time ultrasonic stimulation electric signal recording chip, including the following steps:

S1, manufacturing an interdigital electrode on a piezoelectric substrate to obtain a surface acoustic wave chip, and manufacturing a recording electrode and an electrode lead;

S2, manufacturing an insulation protection layer on the chip obtained in the S1, and processing the insulation protection layer to form the recording electrode, so as to obtain a chip combining the interdigital electrode and the recording electrode;

S3, preparing a PDMS cavity; and

S4, bonding the PDMS cavity prepared in the S3 and the chip obtained in the S2, so as to obtain the real-time ultrasonic stimulation electric signal recording chip.

Preferably, in the S1, the manufacturing of the interdigital electrode on the piezoelectric substrate to obtain the surface acoustic wave chip specifically includes:

patterning photoresist on the piezoelectric substrate through photo etching, then forming a metal layer on the patterned piezoelectric substrate through magnetron sputtering, and removing the photoresist, so as to obtain the surface acoustic wave chip.

Preferably, the S1 specifically includes:

S11, gluing: spin coating photoresist with the thickness of 1-5 µm on a surface of the piezoelectric substrate, and heating;

S12, exposing and developing: covering a manufactured film on the photoresist for exposing, then adopting a developing solution for developing, so as to carry out the patterning on the photoresist;

S13, sputtering: performing the magnetron sputtering on the patterned piezoelectric substrate to form the metal layer, so as to obtain a piezoelectric substrate of a growth electrode;

S14, removing the photoresist: carrying out ultrasonic cleaning on the piezoelectric substrate of the growth electrode obtained in the S13 in an acetone solution, and stripping the photoresist, so as to obtain the surface acoustic wave chip.

Preferably, the photoresist in the S11 is a positive photoresist AZ5214, and conditions of the spin coating are: rotation rate of 3000 rpm, and time of 30 s; and the film in the S12 is a film, and the developing solution is mif300.

Preferably, the S2 specifically includes:

S21, sputtering: manufacturing the insulation protection layer on the surface acoustic wave chip obtained in the S1 by means of sputtering;

S22, processing: spin coating the photoresist on the insulation protection layer, covering the manufactured film on the photoresist and exposing, then adopting the developing solution for developing, and etching to form the recording electrode, so as to obtain the chip combining the interdigital electrode and the recording electrode.

Preferably, the photoresist in the S22 is a negative photoresist SUN1300, and the conditions of the spin coating are: the rotation rate of 3000 rpm, and the time of 30 s; and the film is a film.

In a specific implementation, the insulation protection layer is selected from at least one of silicon dioxide, photoresist, polyimide and silicon nitride, that is, any one of the above materials is adopted to prepare the insulation protection layer, which is applicable to the present invention.

Preferably, in the S3, preparing the PDMS cavity specifically includes:
manufacturing a PDMS cavity mold, casting PDMS in the PDMS cavity mold, and stripping after the PDMS is solidified, so as to obtain a PDMS cavity;
where the PDMS cavity mold is manufactured by means of three dimensional printing.

Preferably, in the S4, a specific process of the bonding the PDMS cavity and the chip is as follows:
carrying out a plasma treatment on the PDMS cavity and the chip, then bonding the two, and baking at 80° C. for 20 min, so as to obtain the real-time ultrasonic stimulation electric signal recording chip;
where the conditions of the plasma treatment: power of 150 W, and time of 70 s.

Preferably, in the S1, the piezoelectric substrate is a 128° YX double-sided polished lithium niobate substrate, a zinc oxide substrate or an aluminum nitride substrate.

The present invention also protects the real-time ultrasonic stimulation electric signal recording chip prepared by the above preparation method.

The present invention has the following beneficial effects.

1. The present invention combines the interdigital electrode with the recording electrode, that is, combines the interdigital electrode generating the surface acoustic wave ultrasound with a multi-channel recording electrode, such that real-time recording of a multi-channel electric signal under ultrasonic stimulation is achieved, the real-time recording of a plurality of neuron electric signals on a neural loop can be achieved, and a mechanism of ultrasonic neuromodulation can be studied from the neural loop; moreover, the chip of the present invention does not increase in size compared to a commercial multi-channel recording electrode, effectively avoiding a problem that a traditional transducer is incompatible with the multi-channel recording electrode due to overlarge volume.

2. The relative position of the interdigital electrode and a neuron cell at a recording electrode position in the chip of the present invention is fixed, such that the energy received by the cell is the same under the same parameter, the repeatability of the experiment is ensured, and the accuracy of the neuron electric signal recording is ensured.

3. Through the setting of the PDMS cavity, the neuron cell or brain piece can be placed in the PDMS cavity for cultivation, the recording of the long-term ultrasonic stimulation and electric signal can be achieved, and the long-time effect of the ultrasound can be studied.

DETAILED DESCRIPTION OF THE EMBODIMENTS

In order to make the objectives, technical solutions and advantages of the present invention more clearly understood, the present invention is further described in detail below with reference to the embodiments. It should be understood that the specific embodiments described herein are only used to illustrate the present invention, but not to limit the present invention.

Embodiment 1

Figure 1:
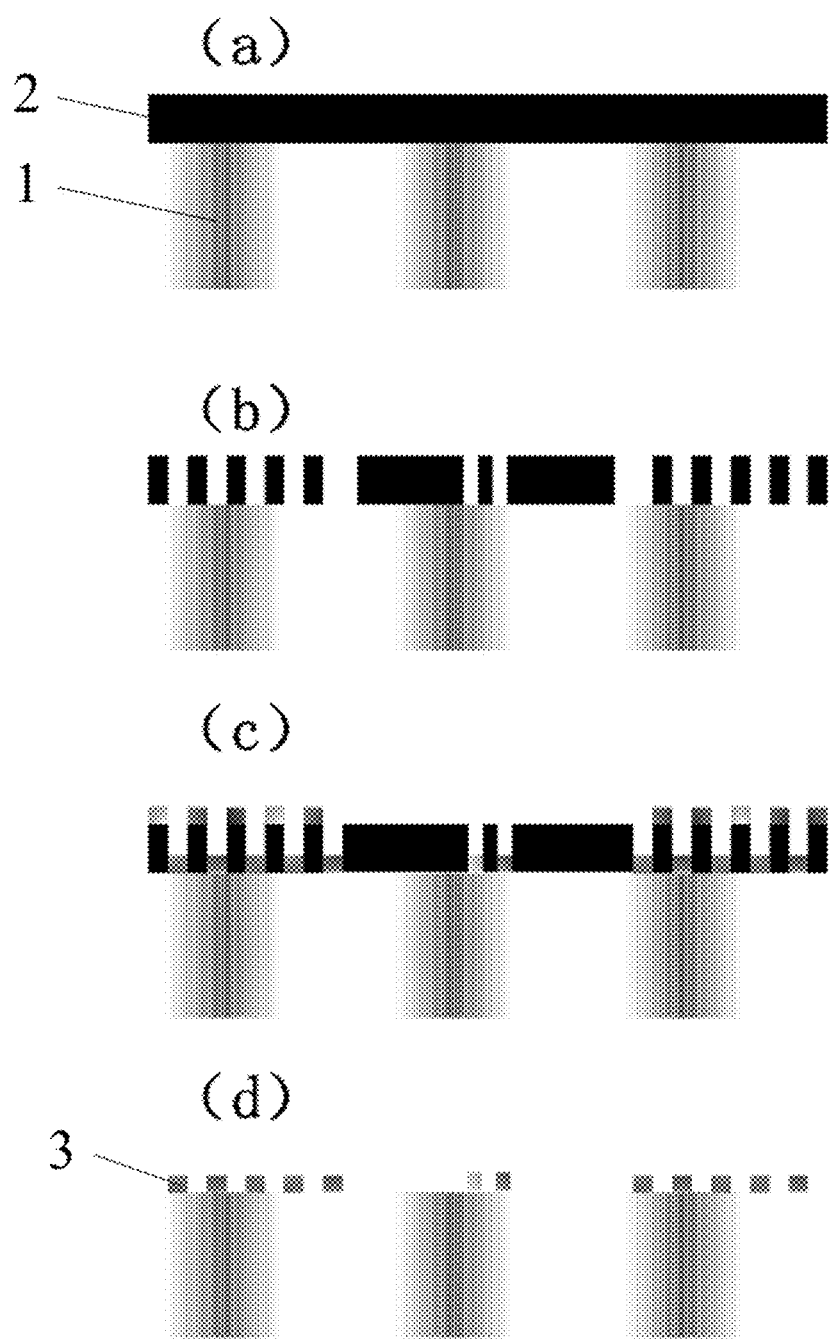
FIG. 1 is a preparation process diagram of a surface acoustic wave chip in a preparation method for a real-time ultrasonic stimulation electric signal recording chip according to embodiment 1 of the present invention;
In the figure: (a) is a process of gluing a piezoelectric substrate; (b) is a process of exposing and developing; (c) is a process of sputtering; and (d) is a process of removing a photoresist to obtain the surface acoustic wave chip.
Figure 2:
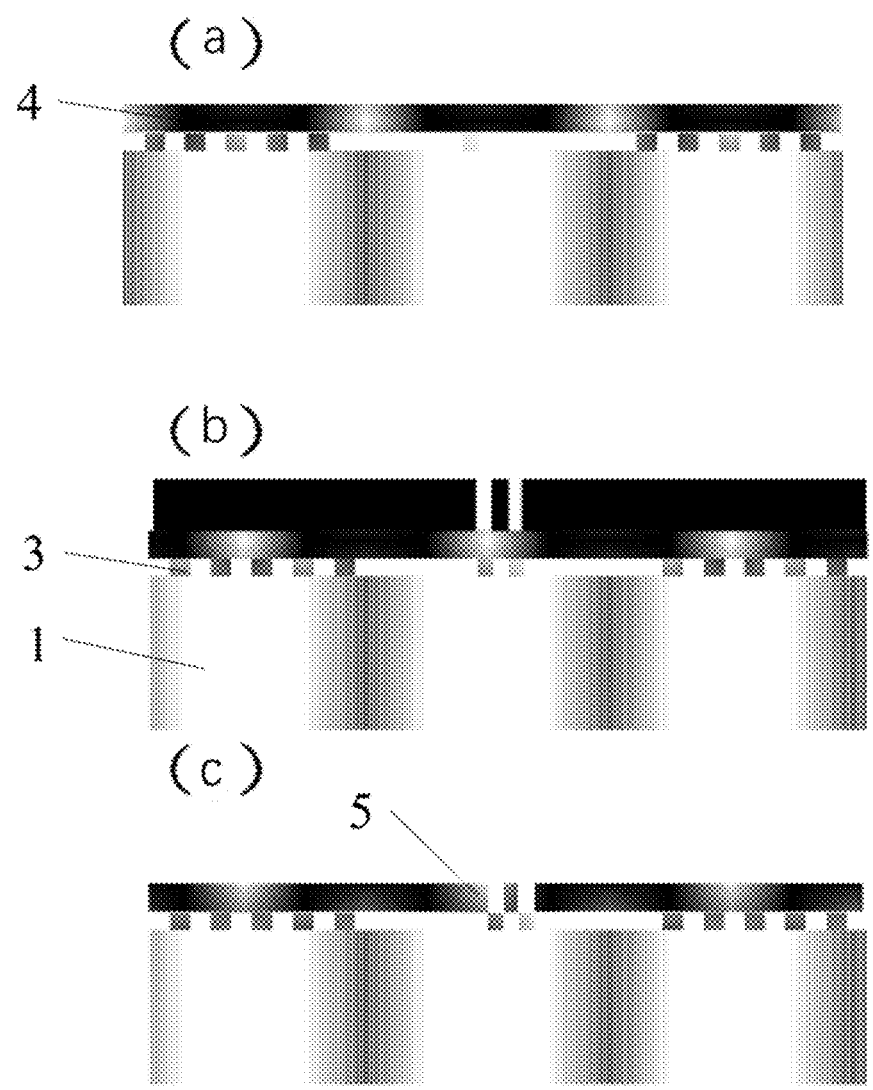
FIG. 2 is a preparation process diagram of a chip in which an interdigital electrode and a recording electrode are combined in a preparation method for a real-time ultrasonic stimulation electric signal recording chip according to embodiment 1 of the present invention;
In the figure: (a) is a process of sputtering an insulation protection layer; (b) is a process of gluing, exposing and developing; and (c) is a process of etching.
Figure 3:
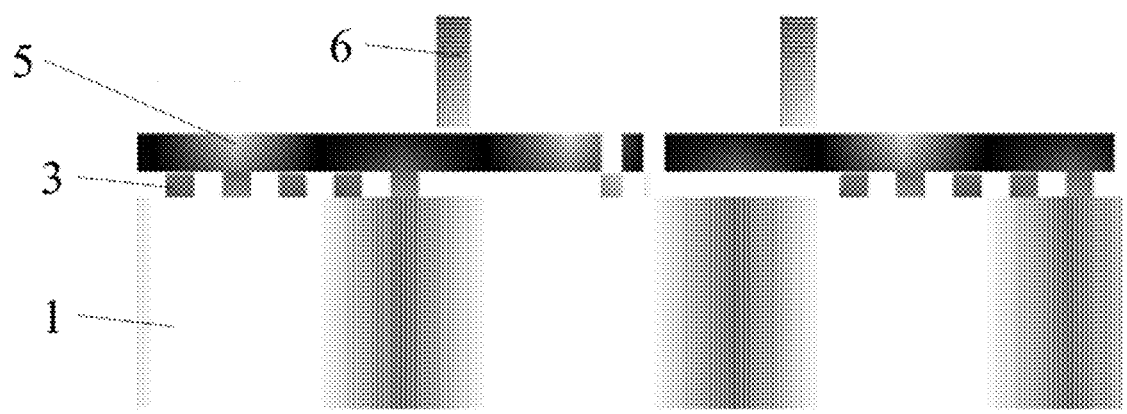
FIG. 3 is a preparation process diagram of bonding a PDMS cavity and a chip in a preparation method for a real-time ultrasonic stimulation electric signal recording chip according to the present invention 1;
In the figure: 1. a piezoelectric substrate; 2. photoresist; 3. a combination of an interdigital electrode and a recording electrode; 4. an insulation protection layer; 5. an etched insulation protection layer; 6. a PDMS cavity.

The present embodiment provides a preparation method for a real-time ultrasonic stimulation electric signal recording chip, as shown in FIGS. 1 to 3, including the following steps.

S1, manufacturing an interdigital electrode on a piezoelectric substrate 1 to obtain a surface acoustic wave chip, and manufacturing a recording electrode and an electrode lead.

It specifically includes:
S11, gluing: spin coating a positive photoresist AZ5214 on a surface of the completely and clearly cleaned piezoelectric substrate 1 at 3000 rpm for 30 s to obtain photoresist 2 with the thickness of 1-5 μm shown in FIG. 1(a), and baking on a heating plate at 65° C. for 3 min;
where the piezoelectric substrate 1 is a 128° YX double-side polished lithium niobate substrate;
S12, exposing and developing: covering the manufactured film on the photoresist 2 shown in FIG. 1(a) for exposing, where a part with a pattern is opaque, a part without a pattern is transparent, and a part with the light transmission is solidified, and then when mif300 is used for developing, the solidified part is dissolved, the non-solidified part is not dissolved, and a graph shown in the FIG. 1(b) is formed by developing;
S13, sputtering: performing magnetron sputtering on the patterned piezoelectric substrate 1 to form a metal layer with the thickness of 200 nm, so as to obtain a piezoelectric substrate of a growth electrode, as shown in FIG. 1(c);
S14, removing the photoresist: carrying out ultrasonic cleaning on the piezoelectric substrate of the growth electrode obtained in the S13 in an acetone solution, and stripping the photoresist, so as to obtain the surface acoustic wave chip, as shown in FIG. 1(d).

S2, manufacturing an insulation protection layer 4 on the chip obtained in the S1, that is, a silicon dioxide layer, and processing the insulation protection layer 4 to form a recording electrode, so as to obtain a chip combining the interdigital electrode with the recording electrode, that is, the chip including a combination 3 of the interdigital electrode and the recording electrode, as shown in FIG. 2.

It specifically includes:

S21, sputtering: cleaning the prepared chip, and preparing the insulation protection layer 4 by means of sputtering, as shown in FIG. 2(*a*);

S22, processing: spin coating a negative photoresist SUN1300 on a surface of the completely cleaned chip at 3000 rpm for 30 s, then covering the manufactured film on the surface for exposing, where a part with a pattern is opaque, a part without a pattern is transparent, and a part with light transmission is solidified, and the solidified part is dissolved and the non-solidified part is not dissolved when developing, and through a design of the film, a solvent part is a recording electrode position, as shown in FIG. 2(*b*); and etching the insulation protection layer on the surface of the chip by means of etching, etching the protection layer at a position without the photoresist, so as to obtain an etched insulation protection layer 5, and displaying the recording electrode for recording an electric signal, as shown in FIG. 2(*c*).

S3, preparing a PDMS cavity 6.

It specifically includes:

S31, printing a PDMS cavity mold through three dimensions;

S32, casting PDMS: mixing a glue A and a glue B of the PDMS according to a mass ratio of 10:1, uniformly mixing, pouring into a mold, vacuumizing to remove air bubbles in the PDMS, and finally placing a glass garden in an oven at 80° C. for 30 min to solidify the PDMS;

S33, stripping: stripping the PDMS cavity 6.

S4, bonding the PDMS cavity 6 prepared in the S3 and the chip obtained in the S2, so as to obtain the real-time ultrasonic stimulation electric signal recording chip.

It specifically includes: carrying out a plasma treatment on the chip manufactured in the S2 and the PDMS cavity 6 manufactured in the S3, where the power of the plasma treatment is 150 W, the duration is 70 s, then adhering the PDMS cavity 6 on the chip for bonding, and baking in an oven at 80° C. for 20 min, so as to obtain the manufactured real-time ultrasonic stimulation electric signal recording chip for the experiment shown in FIG. 3.

The present embodiment further provides the real-time ultrasonic stimulation electric signal recording chip prepared by the above preparation method.

Embodiment 2

A real-time ultrasonic stimulation electric signal recording chip and a manufacturing method thereof of the present embodiment are the same as those of embodiment 1, except that a piezoelectric substrate in S1 is a zinc oxide substrate during the preparation of the present embodiment.

Embodiment 3

A real-time ultrasonic stimulation electric signal recording chip and a manufacturing method thereof of the present embodiment are the same as those of embodiment 1, except that a piezoelectric substrate in S1 is an aluminum nitride substrate during the preparation of the present embodiment.

Embodiment 4

A real-time ultrasonic stimulation electric signal recording chip and a preparation method thereof of the present embodiment are the same as those of embodiment 1, except that an insulation protection layer in S2 is photoresist during the preparation of the present embodiment.

Embodiment 5

A real-time ultrasonic stimulation electric signal recording chip and a preparation method thereof of the present embodiment are the same as those of embodiment 1, except that an insulation protection layer in S2 is polyimide during the preparation of the present embodiment.

Embodiment 6

A real-time ultrasonic stimulation electric signal recording chip and a manufacturing method thereof of the present embodiment are the same as those of embodiment 1, except that an insulation protection layer in S2 is silicon nitride during the preparation of the present embodiment.

In specific implementation, specific processes, such as spin coating time, thickness, baking time, photoresist, developing solution, and film, in the above embodiments of the present invention are only used for explaining the embodiments, and do not limit the present invention; specific conditions of the spin coating time, the thickness and the like of the present invention can be adjusted according to the actual requirements, other specific conditions which accord with the preparation method of the present invention are all suitable for the present invention, and the preparation method and/or the prepared real-time ultrasonic stimulation electric signal recording chip of the present invention belong to the protection scope of the present invention.

The above are only preferred embodiments of the present invention, but the protection scope of the present invention is not limited to this. Any changes or substitutions that can be easily thought of by those familiar with the technical field within the technical scope disclosed by the present invention should fall within the protection scope of the present invention. Therefore, the protection scope of the present invention should be subject to the protection scope of the claims.

What is claimed is:

1. A preparation method for a real-time ultrasonic stimulation electric signal recording chip, comprising the following steps:

S1, manufacturing an interdigital electrode on a piezoelectric substrate to obtain a surface acoustic wave chip, and manufacturing a recording electrode and an electrode lead;

S2, manufacturing an insulation protection layer on the chip obtained in the S1, and processing the insulation protection layer to form the recording electrode, so as to obtain a chip combining the interdigital electrode and the recording electrode;

S3, preparing a PDMS cavity; and

S4, bonding the PDMS cavity prepared in the S3 and the chip obtained in the S2, so as to obtain the real-time ultrasonic stimulation electric signal recording chip.

2. The preparation method for the real-time ultrasonic stimulation electric signal recording chip according to claim 1, wherein in the S1, the manufacturing of the interdigital electrode on the piezoelectric substrate to obtain the surface acoustic wave chip, specifically comprising:

patterning photoresist on the piezoelectric substrate through photo etching, then forming a metal layer on the patterned piezoelectric substrate through magnetron sputtering, and removing the photoresist, so as to obtain the surface acoustic wave chip.

3. The preparation method for the real-time ultrasonic stimulation electric signal recording chip according to claim 2, wherein the S1 specifically comprises:
- S11, gluing: spin coating photoresist with the thickness of 1-5 μm on a surface of the piezoelectric substrate, and heating;
- S12, exposing and developing: covering a manufactured film on the photoresist for exposing, then adopting a developing solution for developing, so as to carry out the patterning on the photoresist;
- S13, sputtering: performing the magnetron sputtering on the patterned piezoelectric substrate to form the metal layer, so as to obtain a piezoelectric substrate of a growth electrode;
- S14, removing the photoresist: carrying out ultrasonic cleaning on the piezoelectric substrate of the growth electrode obtained in the S13 in an acetone solution, and stripping the photoresist, so as to obtain the surface acoustic wave chip.

4. The preparation method for the real-time ultrasonic stimulation electric signal recording chip according to claim 3, wherein the photoresist in the S11 is a positive photoresist AZ5214, and conditions of the spin coating are: rotation rate of 3000 rpm, time of 30 s; and
the film in the S12 is a film, and the developing solution is mif300.

5. The preparation method for the real-time ultrasonic stimulation electric signal recording chip according to claim 1, wherein the S2 specifically comprises:
- S21, sputtering: manufacturing the insulation protection layer on the surface acoustic wave chip obtained in the S1 by means of sputtering;
- S22, processing: spin coating the photoresist on the insulation protection layer, covering the manufactured film on the photoresist and exposing, then adopting the developing solution for developing, and etching to form the recording electrode, so as to obtain the chip combining the interdigital electrode and the recording electrode.

6. The preparation method for the real-time ultrasonic stimulation electric signal recording chip according to claim 5, wherein the photoresist in the S22 is a negative photoresist SUN1300, and the conditions of the spin coating are: the rotation rate of 3000 rpm, and the time of 30 s; and the film is the film.

7. The preparation method for the real-time ultrasonic stimulation electric signal recording chip according to claim 1, wherein in the S3, the preparing the PDMS cavity specifically comprises:
manufacturing a PDMS cavity mold, casting PDMS in the PDMS cavity mold, and stripping after the PDMS is solidified, so as to obtain a PDMS cavity;
wherein the PDMS cavity mold is manufactured by means of three dimensional printing.

8. The preparation method for the real-time ultrasonic stimulation electric signal recording chip according to claim 1, wherein in the S4, a specific process of the bonding the PDMS cavity and the chip is as follows:
carrying out a plasma treatment on the PDMS cavity and the chip, then bonding the two, and baking at 80° C. for 20 min, so as to obtain the real-time ultrasonic stimulation electric signal recording chip;
wherein the conditions of the plasma treatment: power of 150 W, and time of 70 s.

9. The preparation method for the real-time ultrasonic stimulation electric signal recording chip according to claim 1, wherein in the S1, the piezoelectric substrate is a 128° YX double-sided polished lithium niobate substrate, a zinc oxide substrate or an aluminum nitride substrate.

10. The preparation method according to claim 1, the real-time ultrasonic stimulation electric signal recording chip is prepared and obtained.

* * * * *